United States Patent [19]

Donate et al.

[11] 4,282,386
[45] Aug. 4, 1981

[54] ALKYL, CYCLOALKYL DIETHERS OF (POLY)ALKYLENE GLYCOLS

[75] Inventors: Felipe A. Donate; Zonia G. Cutie, both of Midland, Mich.

[73] Assignee: The Dow Chemical Company, Midland, Mich.

[21] Appl. No.: 145,918

[22] Filed: May 2, 1980

[51] Int. Cl.$^3$ .............................................. C07C 41/05
[52] U.S. Cl. .................................... 568/606; 568/670; 568/609; 568/631; 252; 252/67; 252/578.
[58] Field of Search ............... 568/697, 606, 670, 609, 568/631

[56] References Cited

U.S. PATENT DOCUMENTS

| | | | |
|---|---|---|---|
| 1,968,601 | 7/1934 | Edlund et al. | 568/697 |
| 3,170,000 | 2/1965 | Verdol | 568/697 X |
| 4,187,384 | 2/1980 | Platz et al. | 568/697 X |

FOREIGN PATENT DOCUMENTS 2544569 12/1977 Fed. Rep. of Germany.

OTHER PUBLICATIONS

Evans et al., Industrial and Engineering Chemistry, (1936), vol. 28, No. 10, pp. 1186–1188.

Primary Examiner—Bernard Helfin
Attorney, Agent, or Firm—Douglas N. Deline

[57] ABSTRACT

Mono- and polyalkylene glycol diethers are prepared by reacting the corresponding alkyl monethers with a $C_{5-6}$ cycloalkene in the presence of an acid ion-exchange resin.

4 Claims, No Drawings

ALKYL, CYCLOALKYL DIETHERS OF (POLY)ALKYLENE GLYCOLS

BACKGROUND OF THE INVENTION

U.S. Pat. No. 3,281,475 disclosed a process for forming diethers of polyethylene glycol by reacting tertiary olefins with monoalkyl ethers of polyethylene glycol in the presence of an anhydrous, macroreticular, resinous, polysulfonic acid. Some olefins could not be used in the process. For example, secondary olefins such as propylene and cyclohexene did not react at all or reacted to such a slight extent that it was not possible to detect their formation (column 5, lines 25-37). The products formed nonionic surface active agents which were highly resistant to alkali.

In U.S. Pat. No. 4,187,384 a similar process was disclosed utilizing $C_{3-5}$ alkenes further identified as including propylene and other n-olefins or isobutene (column 2, lines 39-47). There was no disclosure that $C_{5-6}$ cyclic alkenes could be utilized according to the described process. It was also taught that high yields of the desired product were obtained only by lowering the temperature of the reaction to a final temperature of from 40° C. to 80° C. The products formed were useful as aprotic solvents and extractants and as hydraulic fluids.

SUMMARY OF THE INVENTION

The present invention relates to an improved process for preparation of mono- and polyethylene or propylene glycol diethers of the formula

$$R_1-O+(CHR'CHR''O)_n-R_2 \qquad (I)$$

where $R_1$ is phenyl or $C_{1-4}$ alkyl; $R'$ and $R''$ are independently in each alkyleneoxy unit hydrogen or methyl, provided that at most only one of $R'$ or $R''$ is methyl in each alkyleneoxy unit; n is an integer from 1 to 6; and $R_2$ is $C_{5-6}$ cycloalkyl.

The process involves the contacting of cyclopentene or cyclohexene or a mixture of monoolefins containing cyclopentene or cyclohexene with a monoalkyl ether of a mono- or polyethylene or propylene glycol at elevated temperature in the presence of anhydrous acid ion-exchange resin.

By utilizing the conditions of the instant process it has been found that for the first time $C_{5-6}$ cycloalkenes may be utilized to "cap" monoalkyl ethers of alkylene glycols. It has also been found that contrary to the teachings of the prior art substantial amounts of the diether reaction product are not formed except by utilizing the elevated reaction temperatures of the instant process.

DETAILED DESCRIPTION OF THE INVENTION

The monoalkyl ethers used in the process are well-known and are produced by reacting a monohydroxyl-containing compound of the formula $R_1$—OH wherein $R_1$ is as previously defined with ethylene oxide or propylene oxide either separately, sequentially or as a mixture. The reaction generally requires the presence of a catalyst, for example, para-toluene sulfonic acid. Depending on the ratios of the reactants and the conditions of the reaction, monoalkyl ethers of differing degrees of polymerization are produced.

The alkene employed is cyclopentene, cyclohexene or a mixture of 5- and/or 6-carbon alkenes containing at least some of the desired cycloalkene. For commercial reasons of course, it is desirable to utilize as a reactant an alkene stream containing a substantial portion of the desired cyclic alkene reactant. It has been found that the presence of alkadienes detrimentally affects the instant process through the formation of random oligomers that contaminate the catalyst bed and the process equipment.

The catalyst utilized in an anhydrous acidic resin stable at operating temperatures above 100° C. Suitable catalysts include the well-known cross-linked styrene-/divinylbenzene copolymers containing sulfonic acid groups which are preferably prepared so as to be highly porous. Such macroporous resins are well-known and may be produced, for example, according to the procedures of U.S. Pat. Nos. 3,418,262; 3,509,078; 3,551,358; 3,637,535 or 3,586,646. A preferred catalyst however has been found to be a perfluorosulfonic acid polymer in the acid form. An example of such a resin is Nafion ® 511, a granulated perfluorosulfonic acid polymer of 1.0 mm diameter nominal size. The resin is formed by copolymerization of tetrafluoroethylene and various monomers such as perfluoro-3,6-dioxa-4-methyl-7-octene sulfonyl fluoride. The resin is available commercially from E. I. du Pont de Nemours and Company.

Prior to use the resin is treated with a strong acid so as to convert the resin into the acid form. Utilizing this resin it is possible to produce $C_5$ to $C_6$ cycloalkyl capped diethers of formula I in good yield at temperatures of up to about 150° C.

The temperatures employed in the process range from about 100° C. to about 150° C. At temperatures less than about 100° C. it has been found that the reaction does not occur or occurs too slowly to be practical. At temperatures above about 150° C. severe product decomposition results.

Pressures employed are not critical. Preferably autogeneous pressure may be employed. Utilizing normal $C_{5-6}$ cycloalkenes or $C_{5-6}$ hydrocarbon streams comprising $C_{5-6}$ cycloalkenes, pressures from about atmospheric to 7 bars (about 100 psig) may be employed.

Of critical importance to the successful operation of the process is the ability to operate at temperatures in excess of about 100° C. As previously stated it has been found that contrary to prior art processes, elevated temperatures are required for the instant process. The catalysts employed, therefore, must be stable at the desired operating temperatures employed during the reaction.

The contacting of cyclic alkylene and monoether reactants is accomplished in an ordinary manner. For example, the two reactants are combined in the presence of the catalyst in pressure reactors of steel or other ordinary construction. The reactor is then heated for several hours up to 70 hours or longer. After cooling the reaction mixture may be separated from the catalyst by filtration and the desired product separated by fractional distillation.

Conversions based on glycol ether reactant from 50 percent to about 60 percent are generally obtained. Selectivities to the desired dialkyl ether product of about 90 percent may be obtained depending on the catalyst, temperature and reaction time employed.

The compounds having high dielectric constants and low viscosities even at reduced temperatures find utility as dielectric fluids or as heat transfer fluids for transformers or other electrical equipment.

SPECIFIC EMBODIMENTS

The following examples are included as illustrative and are not to be construed as limiting.

EXAMPLE 1

In a 500 ml Parr bomb were placed diethylene glycol monomethyl ether (120 g, 1.0 mole), cyclopentene (75 g, 1.1 mole) and 10 g of anhydrous DOWEX® MSC—1H+ ion-exchange resin, a sulfonated crosslinked styrene/divinyl benzene copolymer prepared by suspension polymerization. The reactor was sealed and heated to a temperature of 100° C.–110° C. for about 48 hours.

After the reaction was completed, the product was analyzed by gas chromatography. Conversion of methyl glycol ether was 50 percent with 90 percent selectivity to [2-(2-methoxyethoxy)ethoxy]cyclopentane.

EXAMPLE 2

Diethylene glycol monoethyl ether (60 g, 0.45 mole), cyclopentene (30.6 g, 0.45 mole) and 4.65 g of Nafion® 511 were placed in a 180 ml rocking bomb and heated. Prior to utilizing the resin it was acidified by contacting with excess 3 M $HNO_3$, rinsed, and dried under reduced pressure. The reaction was continued for about 21 hours at 100° C. Conversion based on glycol ether was found to be 57 percent with 84 percent selectivity to [2-(2-methoxyethoxy)ethoxy]cyclopentane.

EXAMPLE 3

A mixture of mono n-butyl glycol ethers containing 15 percent di-, 53 percent tri- and 32 percent tetraethylene glycol n-butyl ether was reacted with cyclopentene in the presence of Nafion® 511 ion-exchange resin acidified with nitric acid as in Example 2. Accordingly, the monoalkyl glycol ether (155 g), cyclopentene (51 g, 0.75 mole) and resin (9.0 g) were placed in a 300 ml stirred autoclave. The mixture was heated with stirring to 100° C. and maintained for 72 hours. Analysis of the reaction indicated 50 percent conversion of cyclopentene to n-butyl cyclopentyl glycol diether resulted.

EXAMPLE 4

The following diether products were formed according to the procedure employed in Example 2 and tested for properties as dielectric fluids. In particular specific applications involving low temperatures are preferred in order to utilize the compounds' low viscosity even at temperatures of −40° C. The following table illustrates these properties.

| Compound | Boiling Point | Dielectric Constant | Viscosity −40° C. (cSt) |
|---|---|---|---|
| 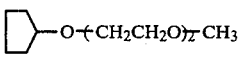—O$(CH_2CH_2O)_2$CH$_3$ | 80° C. (1.0mm) | 5.7 | 27 |
| 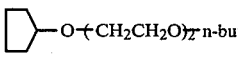—O$(CH_2CH_2O)_2$n-butyl | 85° C. (0.2mm) | 4.4 | 39 |
| 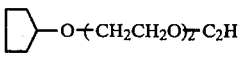—O$(CH_2CH_2O)_2$C$_2$H$_5$ | 70° C. (0.1mm) | — | 32 |
| 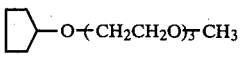—O$(CH_2CH_2O)_3$CH$_3$ | 125° C. (0.2mm) | 6.9 | 75 |

What is claimed is:

1. A process for production of a glycol diether of the formula $R_1O(CHR'CHR''O)_nR_2$ where $R_1$ is phenyl or $C_{1-4}$ alkyl; $R'$ and $R''$ are independently in each alkyleneoxy unit hydrogen or methyl, provided that at most only one of $R'$ or $R''$ is methyl in each alkyleneoxy unit; n is an integer from 1 to 6; and $R_2$ is $C_{5-6}$ cycloalkyl by reacting one or more glycol monoalkyl ethers of the formula $R_1O(CHR'CHR''O)_nH$ where $R_1$, $R'$, $R''$ and n are as previously defined with cyclopentene or cyclohexene in the presence of a synthetic ion-exchange resin in the acid form at a temperature from about 100° C. to about 150° C. under autogenous pressure for a time sufficient to form the desired product.

2. The process of claim 1 wherein the cycloalkene is cyclopentene.

3. The process of claim 1 wherein the glycol monoalkyl ether is a (poly)ethylene glycol monoalkyl ether.

4. The process of claim 1 wherein the synthetic ion-exchange resin is a perfluorosulfonic acid resin in the acid form.

* * * * *

UNITED STATES PATENT AND TRADEMARK OFFICE
CERTIFICATE OF CORRECTION

PATENT NO. : 4,282,386
DATED : August 4, 1981
INVENTOR(S) : Felipe A. Donate and Zonia G. Cutie It is certified that error appears in the above—identified patent and that said Letters Patent is hereby corrected as shown below:

ON THE TITLE PAGE:
In the Abstract, line 2, "monethers" should read --monoethers--.

Column 2, line 8, "in" should read --is--.

Column 2, line 17, "3,637;535" should read --3,637,535--.

Column 2, line 28, "$C_5$ to $C_6$" should read --$C_5$ or $C_6$--.

Column 4, line 15, the first line of the third column of the table "5.7 27" should read --5.7-- and the first line of the fourth column should read --27--.

Signed and Sealed this

Twenty-fourth Day of November 1981

[SEAL]

Attest:

GERALD J. MOSSINGHOFF

*Attesting Officer*     *Commissioner of Patents and Trademarks*